US006991817B2

(12) United States Patent
An et al.

(10) Patent No.: US 6,991,817 B2
(45) Date of Patent: Jan. 31, 2006

(54) ACID-MODIFIED ARABINOGALACTAN PROTEIN COMPOSITION

(75) Inventors: Jinhua An, Palo Alto, CA (US); Karen S. Leu, Saratoga, CA (US); Edwin S. Lennox, Standford, CA (US); John H. Musser, San Carlos, CA (US)

(73) Assignee: Pharmagenesis, Inc., Palo Alto, CA (US)

( * ) Notice: Subject to any disclaimer, the term of this patent is extended or adjusted under 35 U.S.C. 154(b) by 182 days.

(21) Appl. No.: 10/296,935

(22) PCT Filed: Jun. 28, 2001

(86) PCT No.: PCT/US01/20828

§ 371 (c)(1),
(2), (4) Date: Nov. 27, 2002

(87) PCT Pub. No.: WO02/02607

PCT Pub. Date: Jan. 10, 2002

(65) Prior Publication Data

US 2003/0211077 A1 Nov. 13, 2003

Related U.S. Application Data

(60) Provisional application No. 60/215,365, filed on Jun. 29, 2000.

(51) Int. Cl.
*A61K 35/78* (2006.01)
(52) U.S. Cl. ..................................... 424/773; 424/725
(58) Field of Classification Search ................. 424/773
See application file for complete search history.

(56) References Cited

U.S. PATENT DOCUMENTS

| | | | | |
|---|---|---|---|---|
| 4,708,949 A | * | 11/1987 | Liu | 514/26 |
| 4,795,742 A | * | 1/1989 | Liu | 514/26 |
| 4,843,067 A | | 6/1989 | Liu | 514/54 |
| 4,944,946 A | | 7/1990 | Liu | 424/195.1 |
| 4,950,751 A | | 8/1990 | DeWitt | 536/128 |
| 5,116,969 A | | 5/1992 | Adams et al. | 536/128 |
| 5,268,467 A | | 12/1993 | Verbiscar | 536/123 |
| 5,336,506 A | | 8/1994 | Josephson et al. | 424/488 |
| 5,478,576 A | | 12/1995 | Jung et al. | 424/488 |
| 5,554,386 A | | 9/1996 | Groman et al. | 424/488 |
| 5,589,591 A | | 12/1996 | Lewis | 536/128 |
| 5,646,029 A | | 7/1997 | Chen et al. | 435/325 |
| 5,679,323 A | | 10/1997 | Menz et al. | 424/322 |
| 5,756,098 A | | 5/1998 | Price et al. | 424/195.1 |
| 5,770,217 A | | 6/1998 | Kutilek, III et al. | 424/442 |
| 5,830,747 A | | 11/1998 | Chen et al. | 435/252.3 |

FOREIGN PATENT DOCUMENTS

| | | |
|---|---|---|
| EP | 0 441 278 A1 | 8/1991 |
| EP | 0 511 932 A2 | 11/1992 |
| EP | 0 668 072 A1 | 8/1995 |
| WO | WO 01/00682 | 1/2001 |

OTHER PUBLICATIONS

Larm, O. et al.; "Structured Studies on a Water-soluble Arabinogalactan Isolated from Rapeseed (*Brassica napus*)," 1976, Acta Chemica Scandinavica B 30:627-630.*
Dissertation Abstract International, "Identification of Immunostimulants Derived from Astragalus Membranaceus", vol. 47, No. 7, Jan. 1987, pp. 2991. Abstract of dissertation of Michael A. McLauhglin.
Database Chemical Abstracts, Online, Chemical Abstracts Service, Columbus OH/US; AN 115:105995, XP002150924 abstract, Nov. 28, 1990. Abstract of Chinese Patent No. 1047296.
Dan Bensky et al., "Radix Astragali", *Chinese Herbal Medicine, Materia Medica*, Sixth printing 1991, pp. 457-459.
Hson-Mou Chang et al., "Huangqi", *Pharmacology and Applications of Chinese Materia Medica*, 1987, vol. II, pp. 1041-1046.
Da-Tong Chu et al., "Immunotherapy with Chinese Medicinal Herbs II. Reversal of Cyclophosphamide-Induced Immune Suppression by Administration of Fractionated *Astragalus membrane aceus* In Vivo", *J. Clin. Lab. Immunology*, 1988, pp. 25:125-129.
Da-Tong Chu et al., "Fractionated Extract of *Astragalus membranaceus*, A Chinese Medicinal Herb, Potentiates lak Cell Cytotoxicity Generated by a Low Dose of Recombinant Interleukin-2", *J. Clin. Lab. Immunology*, 26, 1988, pp. 4:183-187.
Quan H.X. et al., "Effects of *Astragalus membranaceus* on Irradiated Animal", *Zhong Cao Yao Zazhi*, 1993, pp. 24: 423-425. No translation available.

(Continued)

*Primary Examiner*—Susan Coe
*Assistant Examiner*—S. B. McCormick-Ewoldt
(74) *Attorney, Agent, or Firm*—James A. Fox; Heller Ehrman LLP

(57) ABSTRACT

An acid-modified arabinogalactan protein composition, having an arabinose-galactaose ratio of less than 3.5:1, comprising 5–10% Rha, 20–35% Gal, and less than 5% Glc, prepared from *Astragalus membranaceus*, is useful for treating a number of conditions. For example, an acid-modified arabinogalactan protein composition having features of the invention is useful for stimulating hematopolesis, inducing the proliferation of megakaryocytes, inducing the maturation of megakaryocytes, and stimulating the production of IL-1β, IL-6, TNF-α, IFN-γ, GM-CSF, G-CSF, and neutrophils, and stimulating the action of neutrophils; stimulating the immune and/or hematopoietic system of a mammal suffering from neutropenia, anemia, thrombocytopenia, exposure to cytotoxic agents, exposure to radiation, cachexia, emesis, and drug withdrawal symptoms; and is effective to restore the immune response to infection, in immunosuppressive conditions, and to protect hepatic cells in hepatitis B.

24 Claims, No Drawings

OTHER PUBLICATIONS

Dr. Hong-Yen Hsu, "Astragali Radix", *Oriental Materia Medica a Concise Guide*, 1986, pp. 521.

Shin-Ichi Miura et al., "Effect of a Traditional Chinese Herbal Medicine Ren-Shen-Yang-Rong-Tang (Japanese Name: Ninjin-Youei-To) On Hematopoietic Stem Cells In Mice", *Int. J. Immunopharmac.*, vol. 11, 1989, pp. 7:771-780.

Michael A. Mclaughlin, "Identification of Immunostimulants Derived from *Astragalus membranaceus*", PhD Dissertation. Abstracted at document 19.

Eugene A. Nothnagel, "Proteoglycans and Related Components in Plant Cells", *International Review of cytology*, vol. 174, pp. 195-289.

Yoko Ohnishi et al., "Effects of Juzen-taiho-toh (TJ-48), a Traditional Oriental Medicine, on Hematopoietic Recovery from Radiation Injury in Mice", *International Society for Experimental Hematology*, 1990, pp. 18-22.

Ma Rou et al., "The Effect of Radix Astragali on Mouse Marrow Hemopoiesis", *Journal of Traditional Chinese Medicine*, 1983, 3(3): 199-204.

Jin Rui et al., "Effects of Shi-ka-ron and Chinese Herbs in Mice treated with Anti-Tumor Agent Mitomycin C", *Chung-Kuo Chung His i Chieh Ho Tsa Chih* 15, No. 2:101, abstract only, no translation.

Jens Sommer-Knudsen et al., "Hydroxyproline-rich plant glycoproteins", *Phytochemistry*, 1998, vol. 47(4), pp. 483-497.

Yan Sun et al., "Preliminary Observations on the Effects of the Chinese Medicinal Herbs *Astragalus membranaceus* and *Ligustrum lucidum* on Lymphocyte Blastogenic Responses", *Journal of Biological Responses Modifiers*, 1983, vol. 2, pp. 227-237.

W. Tang et al., "*Astragalus membranaceus* (Fisch.) Bge.", *Chinese Drugs of Plant origin*, 1992, pp. 191-197.

Quan, H. X. et al., "Effects of *Astragalus membranaceus* on Hematopoiesis of Irradiated Mice", *Zhongguo Zhongyao Zazhi*, 1994, pp. 19:741-743, no translation.

K.S. Zhao et al., "Enhancement of the Immune Response in Mice by *Astragulus membranaceus*. Extracts", *Immunopharmacolgy* 20, 1990, pp. 3:225-234.

K.W. Zhao et al., "Effect of Astragalan on Secretion of Tumor Necrosis Factors in Human Peripheral Blood Mononuclear Cells", *Chung-Kuo Chung His i Chieh Ho Tsa Chih* 13, No. 5:263-259, abstract only, no translation.

Xiao-sheng, W. et al., "Treatment of Leucopenia with Pure Astragalus Preparation—An Analysis of 115 Leucopenic cases", *Zhongguo Zhongxiyi Jieho Zazhi, Chinese J. Inter. Trad. Western Med.* 15, 1995, pp. 8:462-464, abstract only, no translation.

*Handbook of Instrumental Techniques for Analytical chemistry*, ed. Frank Settle, Chapter 46, pp. 853-866 (chapter author: David Meunier), published by Prentice-Hall, 1997 (ISBN No. 013177380).

* cited by examiner

ACID-MODIFIED ARABINOGALACTAN PROTEIN COMPOSITION

This application claims benefit of provisional application No. 60/215,365, filed Jun. 29, 2000.

BACKGROUND OF THE INVENTION

1. Field of the Invention

This invention relates to arabinogalactans. In particular, this invention relates to an acid-modified arabinogalactan protein composition, having an arabinose:galactose ratio of less than 3.5:1 or less than 80% of the arabinose:galactose ratio of the arabinogalactan protein component of the composition prior to acid modification, prepared from *Astragalus membranaceus*, especially from the roots of *Astragalus membranaceus*.

2. Description of Related Art

Huang-qi, Radix Astragali, is the dried root of *Astragalus membranaceus* Bge. var. *mongholicus* (Bge.) Hsiao or *A. membranaceus* (Fisch.) Bge. (Fabaceae). Huang-qi is a very old and well known drug in traditional Chinese medicine. It is officially listed in the Chinese Pharmacopoeia and used mainly as a tonic and for treatment of nephritis and diabetes. It is commonly used as a decoction or "tea" alone or with other plants in the traditional medicines Shi-ka-ron (a combination with herbs *Lithosperium erythrorhizon* and *Ligusticum wallachii*) and Ren-shen-yang-rong-tang (a combination of twelve herbs including Radix Astragali) [The section entitled "*Astragalus membranaceus* (Fisch.) Bge.", Section 26, pages 191–197, of "Chinese Drugs of Plant Origin", W. Tang and G. Eisenbrand, eds., Springer Verlag, Berlin, 1992].

Huang-qi decoctions, and solutions prepared from the alcohol-precipitated decoction, have also been administered by injection, and are reported to give improvement in the symptoms of gastric and duodenal ulcers and increase the white blood cell count in chronic leukopenia [The section entitled "Huangqi", pages 1041–1046, of "Pharmacology and Applications of Chinese Materia Medica", H.-M. Chang and P. P.-H. But, eds., World Scientific Publishing Co., Singapore, 1987]. Huang-qi decoctions, purified low molecular weight fractions (e.g. 25,000–35,000 MW), and decoctions of herb mixtures containing huang-qi, have also shown activity in restoring the immune system in local xenogeneic graft-versus-host reaction [D.-T. Chu et al., "Immunotherapy with Chinese medicinal herbs. I. . . . ", *J. Clin. Lab. Immunol.*, 25, 119–123 (1988)], reversing cyclophosphamide-induced immune suppression [D.-T. Chu et al., "Immunotherapy with Chinese medicinal herbs. II . . . ", *J. Clin. Lab. Immunol.*, 25, 125–129 (1988)], potentiating LAK cell cytotoxicity generated by rIL-2 [D.-T. Chu et al., "Fractionated extract of *Astragalus membranaceus*.", *J. Clin. Lab. Immunol.*, 25, 183–187 (1988)], enhancing the immune response in immunodepressed mice [K. S. Zhao et al., "Enhancement of the immune response in mice by *Astragalus membranaceus* extracts", *Immunopharmacology*, 20, 225–234 (1990)], stimulating responses in mononuclear cells [Y. Sun et al., "Preliminary observations on the effects of the Chinese medicinal herbs . . . ", *J. Biol. Response Modifiers*, 2, 227–237 (1983)], and stimulating bone marrow hematopoiesis in mice [M. Rou et al., "The effect of radix astragali on mouse marrow hemopoiesis", *J. Trad. Chin. Med.*, 3(3), 199–204 (1983); S.-I. Miura et al., "Effect of a traditional Chinese herbal medicine . . . ", *Int. J Immunopharmacol.*, 7(11), 771–780 (1989); and Y. Ohnishi et al., "Effects of Juzen-taiho-toh (TJ-48) . . . ", *Exp. Hematol.*, 18, 18–22 (1990)].

Liu, U.S. Pat. No. 4,843,067, discloses a pharmaceutical composition containing polysaccharides of huang-qi (stated to be extractable from either *Astragalus membranaceus* Bge. or *Astragahis gummifer* Labillard) and polysaccharides of dankuei. The huang-qi polysaccharides are stated to be extractable by water extraction of a powder of the roots and ethanol precipitation. Verbiscar, U.S. Pat. No. 5,2868,467, discloses immunomodulatory polysaccharide fractions from the plants of *Astragalus tragacantha* (tragacanth), prepared at low temperature to "maintain the integrity of the polysaccharide toward chemical and conformational changes". Josephson et al., U.S. Pat. No. 5,336,506, discloses the use of plant polysaccharides such as arabinogalactans (isolated from larch, *Larix occidentalis*) and mannans to form complexes with therapeutic agents for the targeting of the therapeutic agent to a cell receptor capable of receptor-mediated endocytosis. Adams et al., U.S. Pat. No. 5,116,969, discloses an ultrarefined arabinogalactan product said to be suitable for use in density gradient separation. Jung et al., U.S. Pat. No. 5,478,576, discloses purified arabinogalactans (also from *Larix occidentalis*), degradative products, and modifications thereof, also for use in delivering therapeutic agents to cell receptors capable of receptor-mediated endocytosis. Lewis, U.S. Pat. No. 5,589,591, discloses endotoxin-free polysaccharides, such as arabinogalactans, dextrans, mannans, and gum arabic, prepared from impure forms of these polysaccharides by ultrafiltration through first through a low molecular weight cutoff membrane, keeping the retentate, and then through a high molecular weight cutoff membrane, keeping the filtrate.

Each of these references, however, devotes its attention to the polysaccharides (e.g. arabinogalactans) present in the products, and may even use techniques designed to exclude arabinogalactan proteins.

Arabinogalactan proteins are also found in flowering plants, and are widely distributed in most higher plants. Arabinogalactan proteins (AGPs), sometimes referred to as arabinogalactan peptides, are glycosylated proteins containing high proportions of carbohydrate and usually a low (less than 10%) protein content, although AGPs having a higher protein content are known. Among the hydroxyproline-rich glycoproteins isolatable from plants, AGPs are characterized by their generally low protein content and their general ability to bind the β-glucosyl Yariv reagent, 1,3,5-tris(4-β-D-glucopyranosyloxyphenylazo)-2,4,6-trihydroxybenzene, [J. H. Yariv et al., *Biochem. J.*, 85, 383–388 (1962); R. L. Anderson et al., *Aust. J. Plant Physiol.*, 4, 143–158 (1977)]. AGPs are components of gum arabic, a gummy exudate from the acacia tree, Acacia senegal, that is frequently used in food products as an emulsifier, crystallization preventer, and flavor eincapsulator. The isolation of plant AGP genes from *Nicotiana alata, Nicotiana plumbaginafolia*, and *Pyrus communis* is disclosed in Chen et al., U.S. Pat. No. 5,646,029. An extensive discussion of AGPs may be found in E. A. Nothnagel, "Proteoglycans and related components in plant cells", *Int. Rev. Cytology*, 174, 195–291 (1997).

The disclosures of these and other documents referred to throughout this application are incorporated herein by reference.

SUMMARY OF THE INVENTION

In a first aspect, this invention provides an acid-modified arabinogalactan protein composition, having an arabinose:

galactose ratio of less than 3.5:1, preferably less than 3.0:1, or less than 80% of the arabinose:galactose ratio of the arabinogalactan protein component prior to acid modification, prepared from *Astragalus membranaceus*, especially from the roots of *Astragalus membranaceus*.

In a second aspect, this invention provides an aqueous injectable acid-modified arabinogalactan protein formulation comprising a therapeutically effective amount of the acid-modified arabinogalactan protein composition of the first aspect of this invention and an aqueous injectable excipient.

In a third aspect, this invention provides a method of treating a disease state in a mammal capable of treatment by administration of the acid-modified arabinogalactan protein composition of the first aspect of this invention or the acid-modified arabinogalactan protein formulation of the second aspect of this invention, such as stimulating hematopoiesis, inducing the proliferation or maturation of megakaryocytes, stimulating the production of IL-1$\beta$, IL-6, TNF-$\alpha$, IFN-$\gamma$, GM-CSF, or G-CSF, stimulating the production or action of neutrophils, treating neutropenia, anemia, or thrombocytopenia, accelerating recovery from exposure (e.g. accidental or non-therapeutic exposure, as well as therapeutic exposure) to cytotoxic agents or radiation, treating cachexia, emesis, or drug withdrawal symptoms, or restoring or stimulating immune responses to viral, bacterial, fungal, and other infections and in other immunosuppressive conditions, or protecting hepatic cells in hepatitis B, in a mammal, comprising administering to the mammal an effective amount of the acid-modified arabinogalactan protein composition of the first aspect of this invention, especially as an aqueous injectable acid-modified arabinogalactan protein formulation of the second aspect of this invention; optionally in conjunction with at least one other therapeutic agent (such as one capable of stimulating hematopoiesis).

In a fourth aspect, this invention provides methods of preparing the acid-modified arabinogalactan protein composition of the first aspect of this invention and the acid-modified arabinogalactan protein formulation of the second aspect of this invention.

DETAILED DESCRIPTION OF THE PREFERRED EMBODIMENTS

Definitions

An "acid-modified arabinogalactan protein composition" is an "arabinogalactan protein composition" (as defined below) that has been subject to an acid treatment under such conditions that the composition has an arabinose:galactose ratio of less than 3.5:1, preferably less than 3.0:1, or less than 80% of the arabinose:galactose ratio of the arabinogalactan protein component of the composition prior to acid modification.

An "arabinogalactan protein" or "AGP" is a generally p-glucosyl Yariv reagent-precipitable, highly glycosylated protein in which the carbohydrate accounts for at least 50% by weight of the molecule, and in which the major carbohydrate constituents are arabinose and galactose, with the arabinosyl residues primarily in terminal positions. It generally reacts specifically with a monoclonal antibody, MAC207, for AGPs.

An "arabinogalactan protein composition" is a composition comprising at least 70%, particularly at least 80%, more particularly at least 90%, by weight of the composition of arabinogalactan protein (as defined above) and associated arabinogalactans and other polysaccharides.

"Mammal" includes humans and non-human mammals, such as companion animals (cats, dogs, and the like) and farm animals (cattle, horses, sheep, goats, swine, and the like).

"Disease" includes any unhealthy condition of an animal, including an unhealthy condition resulting from medical therapy (a "side-effect"), such as disease states in which a blood tonifying effect is therapeutic, including particularly those disease states listed in the "Pharmacology and Utility" section of this application.

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

A "therapeutically effective amount" means the amount that, when administered to an animal for treating a disease, is sufficient to effect treatment for that disease.

"Treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

The Acid-Modified Arabinogalactan Protein Composition

The acid-modified arabinogalactan protein composition of this invention is an "acid-modified arabinogalactan protein composition" as that term is defined above that is made from an arabinogalactan protein composition that is isolated from *Astragalus membranaceus*, especially from the roots of *Astragalus membranaceus*; preferably from the roots of *A. membranaceus* Bge. var. *mongholicus* (Bge.) Hsiao or *A. membranaceus* (Fisch.) Bge.; preferably where the roots are from *A. membranaceus* plants grown in Inner Mongolia or Shanxi province, Peoples' Republic of China, especially the former; and preferably where the roots are from two-year-old *A. membranaceus* plants. It has' a typical sugar composition (determined by GLC of the trimethylsilyl derivatives of the methanolyzed composition) containing about between 30 and 60 mole %, particularly about 35–55%, Ara; about between 5 and 10% Rha; about between 5 and 15% GalA; about between 20 and 35% Gal; and less than about 10%, especially less than about 5% Glc; with an Ara:Gal ratio of less than 3.5:1, preferably less than 3.0:1; an ash content of not more than about 2% by weight; a typical heavy metal content of not more than about 20 ppm by weight; and a hydroxyproline content of not more than about 1.0%. It is substantially free of endotoxin (i.e. having an endotoxin content, as determined by Endospecy [Seikagaku Corporation, Tokyo, Japan] assay following the manufacturer's instructions, of less than 1.0 EU/mg, particularly less than 0.8 EU/mg, more particularly less than 0.5 EU/mg, especially less than 0.3 EU/mg); and is soluble in water to at least 200 mg/mL, having a pH in aqueous solution between 4 and 7. For convenience, this material may be referred to further as "AMC".

In a typical preparation of the composition, the glycans comprise approximately 80% by weight of the composition, with proteins and possibly trace amounts of lipids comprising the remainder. The protein core is rich in hydroxyproline, which comprises as much as 25% of the amino acid residues. The acid-modified arabinogalactan protein composition exhibits two size classes by size exclusion chromatography in aqueous solution. The larger size class, comprising approximately 40% by weight of the composition, has a peak molecular weight of approximately 350 kiloDaltons relative to pullulan sizing standards; the smaller size class has a peak molecular weight of approximately 75 kiloDaltons. The weight-average molecular weight computed across the two size classes is about between 120 kiloDaltons and 260 kiloDaltons, for example approximately 200 kiloDaltons, with a calculated polydispersity about between 1 and 5, especially about between 1.5 and 3.5.

Preparation of the Acid-Modified Arabinogalactan Protein Composition

The acid-modified arabinogalactan protein composition is prepared by extracting the *Astragalus membranaceus* (typically the clean processed chipped or sectioned dried roots, prepared by trimming the dried roots, scrubbing with purified water, cleaning with a disinfecting solution such as 70% ethanol, cutting into thin slices, and drying under aseptic conditions, referred to as "drink chips"), with hot water (typically at not less than 80° C., particularly not less than 90° C., especially at about 100° C.), optionally in the presence of a co-extractant such as an alkali metal salt, especially potassium or sodium dihydrogen phosphate (e.g. 0.5 M $KH_2PO_4$ at pH 4.5), for a time, at a temperature, and for as many extraction cycles are necessary or desirable to cause substantial extraction of the arabinogalactan protein and associated polysaccharides from the roots (typically three times each for 3 hours at 100° C.). In a preferred preparation, the drink chips are extracted with an initial hot aqueous salt wash (e.g. in 0.5 M $KH_2PO_4$ at pH 4.5 and 100° C.) for a short time, such as 30 minutes, and the wash is discarded, before the extraction process is performed. All steps following the preparation of the dried comminuted roots are typically conducted under aseptic conditions employing sterile equipment and reagents. The hot water extract is concentrated, such as by evaporation under vacuum at 60–70° C., or simultaneously concentrated and exchanged into water by ultrafiltration (such as by ultrafiltration using a 100 kiloDalton molecular weight cutoff(100K MWCO) ultrafiltration (UF) system), preferred especially if the water for extraction contains a co-extractant, to a concentration of about 1 L/Kg of "drink chips", and then treated to remove materials that are not water-soluble, such as by precipitating with a lower alkanol (e.g. ethanol at an ethanol concentration of about 35%). The supernatant of the lower alkanol precipitation, for example 35% ethanol precipitation, is further precipitated with a higher concentration of lower alkanol, for example 40–80% ethanol, particularly 60–70% ethanol, to precipitate a crude arabinogalactan protein composition containing the arabinogalactan protein and associated polysaccharides. The precipitate may be re-dissolved in water to assist in removal of the lower alkanol and dried (typically by spray drying or freeze drying, to avoid excessive heating) to isolate the crude arabinogalactan protein composition. The crude arabinogalactan protein composition is typically a white to off-white powder.

The crude arabinogalactan protein composition is then acid treated with a suitable acid of suitable concentration, for a suitable time and at a suitable temperature, to reduce the arabinose:galactose ratio of the final acid-modified arabinogalactan protein composition to less than 3.5:1, preferably less than 3.0:1, or to less than 80% of the arabinose:galactose ratio of the arabinogalactan protein component of the composition prior to acid modification. The nature of the acid used and its concentration, and the time and temperature employed for the hydrolysis may be varied considerably from mineral acids, such as hydrochloric acid, used in low concentration at reduced temperature to room temperature for a comparatively short time, to weak organic acids, such as acetic acid, used in high concentrations at elevated temperatures for a long time; however, we have found that trichloroacetic acid, or preferably hydrochloric acid, used at 0.1 to 1 M concentration for 1 to 24 hours, or more (especially at the low concentrations) at slightly elevated temperatures such as room temperature to 40° C., especially around 30° C., is suitable for the hydrolysis. While acid hydrolysis affects arabinose (thereby shortening the polysaccharide sidechains of the arabinogalactan protein) in preference to galactose, care should be taken to ensure sufficient hydrolysis to achieve the desired purification and arabinose:galactose ratio but to avoid excessive hydrolysis, which reduces the yield of active acid-modified arabinogalactan protein composition. Following hydrolysis, the acid solution is neutralized by the addition of a base (e.g. a 0.5 M aqueous alkali metal hydroxide such as sodium hydroxide, or a weak base such as sodium bicarbonate). The resulting solution contains the acid-modified arabinogalactan protein, together with (acid-modified) associated polysaccharides, and quantities of low molecular weight hydrolysis products.

To accommodate batch-to-batch variations in the *Astragalus membranaceus* raw material, blending of the raw material, the "drink chips", and intermediates in the process may be used to achieve consistency of final product.

The solution is then purified by ultrafiltration and ion-exchange chromatography. It is ultrafiltered to further remove salts and low molecular weight materials and to reduce the volume of the solution (such as by using a 100K MWCO UF system). The retentate may be directly dried (such as in a vacuum oven at 60–70° C., or by spray drying or freeze drying, especially in the presence of dissolution enhancing excipients) to give the acid-modified arabinogalactan protein composition or may be further purified, if desired, as described below.

For the optional further purification, the retentate obtained from the ultrafiltration is then eluted through a cation exchange column (such as a SP Sepharose cation exchange column equilibrated with 20 mM NaOAc buffer, pH 5.20); and the eluate loaded onto and eluted through an anion exchange column (such as a Q Sepharose anion exchange column equilibrated with the same NaOAc buffer). The eluate from the anion exchange column is again desalted by ultrafiltration and then dried to give the acid-modified arabinogalactan protein composition.

The order of purification steps may be altered or the steps themselves modified. In particular, the sequential ion-exchange steps chromatography may be replaced by batch treatment of the solution with the same or similar ion-exchange resins, filtering the resins from the treated solution; and the use of separate anion-exchange and cation-exchange resins may be replaced by the use of a mixed-bed resin having both anion- and cation-exchange capability, either as a column or in batch treatment. Also, the ion-exchange treatment may precede the acid modification treatment instead of following it. The use of different UF membranes (such as membranes with lower molecular weight cutoff) for desalting and removal of low molecular weight material is possible. Essential elements of the process are the preparation of the "drink chips", the extraction of an arabinogalactan protein composition therefrom, and acid modification of the arabinogalactan protein composition, and at least one high molecular weight (e.g. 100K MWCO) ultrafiltration step in the process; with variations in the order and nature of the purification steps going more to the yield of the acid-modified arabinogalactan protein composition and ease of performing the preparation than to the nature of the composition so prepared. Of course, if an arabinogalactan protein composition, or especially the >100K fraction of that composition, is prepared by any other method, that composition may be acid modified to give the acid-modified arabinogalactan protein composition.

Pharmacology and Utility

The beneficial activity of the purified arabinogalactan composition of the first aspect of this invention or the arabinogalactan protein composition of the second aspect of this invention have been shown in several tests, leading to the following utilities.

Treatment of Neutropenia in Patients Undergoing Chemotherapy

1. Production of G-CSF from Activated Human Peripheral Blood Mononuclear Cells (PBMC)

Since stimulation of the immune and hematopoietic system occurs via multiple cytokine interactions, the ability of AMC to induce the production of G-CSF in vitro was examined as described in Example 6. AMC triggered significant, dose-dependent release of G-CSF by human PBMC after activation with PHA. G-CSF is known to affect the production/or action of neutrophils in vitro and in vivo. These data suggest that AMC may stimulate production of neutrophils and recovery of platelet counts in myelosuppressed patients via the production of cytokines involved in hematopoietic functions. A similar but weaker response was seen with: (1) a purified arabinogalactan composition (PAGC) that was prepared by extraction of "drink chips", ethanol precipitation, purification by ion exchange chromatography, and further ethanol precipitation; and (2) an arabinogalactan protein composition (AGPC) that was prepared by extraction of "drink chips", ethanol precipitation, purification by ion exchange chromatography, ultrafiltration of the ion-exchange eluate with a 100K MWCO UF membrane keeping the retentate), and further ethanol precipitation. Since PAGC has been shown to stimulate the production of IL-1β, IL-6, TNF-α, IFN-γ, GM-CSF, this and the result above suggest that AMC will do the same.

2. Recovery of GM-CFC Progenitor Cells in Fluorouracil-Treated Mice

PAGC has been shown to enhance bone marrow progenitor (GM-CFC) recovery from fluorouracil-induced myelosuppression in mice; and, based on the results in 1. above, AMC is expected to be at least as potent as PAGC in this assay.

3. Recovery of Peripheral White Blood Cells in sublethally Irradiated Mice

BALB/c mice were sublethally irradiated and then treated subcutaneously with saline or PAGC, AGPC, or AMC according to the protocol described in Example 7. Irradiation dramatically decreased the number of WBC. Treatment with PAGC, AGPC, and AMC increased the total WBC counts to values above those seen in the saline-treated control animals, and increased the rate of recovery of WBC count to not less than $8 \times 10^6$/mL.

4. Restoration of White Blood Cell Counts after Chemotherapy

PAGC has been shown to increase the WBC of human cancer chemotherapy patients over those not given PAGC. Based on the results seen in 1. and 3. above and the comparison with PAGC, AMC is expected to show the same benefit.

Treatment of Thrombocytopenia in Patients undergoing Chemotherapy

1. Recovery of Peripheral Blood Platelet Counts in Sublethally Irradiated Mice

BALB/c mice were sublethally irradiated on day 0 and then treated subcutaneously with saline or AMC, as described in Example 7. Irradiation dramatically decreased the number of platelets. Subcutaneous AMC treatment at 50, 100, and 250 mg/Kg significantly enhanced platelet recovery in the peripheral blood of the mice. These findings suggest that AMC is a highly efficacious agent for enhancing platelet development and should be considered useful for the treatment of thrombocytopenia. AGPC and PAGC were also active in this assay.

2. Proliferation/Maturation of Bone Marrow Megakaryocytes

PAGC has been shown to promote the proliferation and/or maturation of bone marrow megakaryocytes in vitro, and to synergize with a suboptimal dose of IL-3; and, based on the results in 1. above, AMC is expected to be at least as potent as PAGC in this assay. Since chemotherapy or radiation therapy will damage many cells and tissues including cytokine-producing cells, patients so treated may have lower levels of endogenous cytokine secretion. Such low levels of endogenous cytokines may not support the normal functions of the hematopoietic system, which therefore cannot generate adequate numbers of hematopoietic cells for recovery from bone marrow suppression. PAGC has been shown to enhance the proliferation/maturation of bone marrow megakaryocytes to a normal level in the presence of otherwise insufficient levels of endogenous cytokines and stimulate the recovery of peripheral blood platelets and seems to do so by inducing the proliferation and/or the maturation of megakaryocytes. The data suggest that AMC may also prove useful in the treatment of thrombocytopenia that occurs secondary to bone marrow suppression.

3. Increase of Platelet Counts after Chemotherapy

PAGC has been shown to increase the platelet counts of human cancer chemotherapy patients; and, based on the results of 1. above and the comparison with PAGC, AMC is expected to show the same benefit.

Improvement of Quality-of-Life of Cancer Patients

PAGC has been shown to more rapidly increase the rate of recovery from chemotherapy-induced symptoms (lassitude and fatigue, malaise, sweating, shortness of breath and lack of appetite) and increase Karnovsky Performance Index scores, in human chemotherapy patients; and, based on the results above and the comparison with PAGC, AMC is expected to show the same benefit.

Prevention of Neutropenia in Cancer Patients undergoing Chemotherapy

In a prior section, AMC was shown effective for treatment of chemotherapy-induced neutropenia. The data suggest also that AMC may be useful in the prevention of neutropenia as well as in the treatment of neutropenia.

Treatment of Neutropenia in Cancer Patients undergoing Radiation Therapy

The data given previously also suggest the use of AMC for the recovery of neutropenia in radiation therapy.

Treatment of Anemia in Cancer Patients undergoing Chemotherapy

BALB/c mice were sublethally irradiated and then treated with saline or various doses of AMC according to the protocol described in Example 6. Irradiation dramatically decreased the number of RBC. AMC treatment resulted in higher RBC counts. These results indicate that AMC may affect erythroid progenitor cell development and/or mobilization, suggesting its usefulness in radiotherapy- and chemotherapy-induced anemia. PAGC and AGPC are also active in this model.

Mobilization of Peripheral Blood Progenitor Cells Alone or in Combination with G-CSF for Patients undergoing Peripheral Blood Progenitor Cell Transplantation The CD34 antigen is present on hematopoietic stem cells and progenitor cells, including colony-forming cells such as BFU-E (burst-forming unit—erythroid), GM-CFC (granulocyte macrophage colony forming cells), and CFU-Mix (colony forming unit—mixture) cells. The assay by flow cytometry of $CD34^+$ cells provides a convenient determination of graft composition. The existence of hematopoietic progenitor cells in the peripheral blood of humans was first described in 1975. These peripheral blood progenitor cells (PBPC) make up only a small fraction of the total number, since the vast majority of progenitors reside in the bone marrow. Increases in the numbers of peripheral blood progenitor cells in humans during the rebound following chemotherapy were reported in 1976. More recently, the colony stimulating factors G-CSF and GM-CSF have been demonstrated to directly augment the numbers of PBPC. The combination of chemotherapy and colony stimulating factors greatly increases the numbers of PBPC above increases observed with either method alone. Currently, G-CSF is used in humans to mobilize PBPC for autologous and allogeneic transplantation. Transplantation of PBPC leads to more rapid engraftment than conventional bone marrow transplantation. The yield of PBPC generated with G-CSF treatment can be greatly enhanced when used in combination either with chemotherapy, as mentioned above, or with other cytokines. PAGC has been shown to induce PBPC mobilization when administered as a single agent and/or to synergize with G-CSF to induce PBPC mobilization when administered in combination with G-CSF. In a similar experiment with cyclophosphamide-treated mice, an increase in the number of $CD34^+Lin^-$ cells was seen over mice not treated with PAGC. Based on the results above and the comparison with PAGC, AMC is expected to be active in this assay. Therapeutic agents such as AMC which synergize with G-CSF to increase the yields of PBPC will likely be very useful. This type of synergy may reduce costs by decreasing the number of aphereses necessary to harvest PBPC from donors. Additionally, this type of combination therapy may help in situations where recipients are not sufficiently responsive to G-CSF alone or where the use of chemotherapeutic drugs is not desirable.

Acceleration of Healing from Exposure to Cytotoxic Agents or Radiation

From the results and the studies with PAGC given above, where animals or human patients were deliberately exposed to radiation or cytotoxic agents and demonstrated an accelerated healing over animals or human patients not so treated, AMC will also be useful in accelerating recovery from exposure (e.g. accidental or non-therapeutic exposure, as well as therapeutic exposure) to cytotoxic agents or radiation.

Treatment of Cachexia

One of the most common side effects of chemotherapy and radiation therapy is that patients suffer from lack of appetite and weight loss. PAGC has been shown to increase the body weight of mice treated with the chemotherapeutic agents cyclophosphamide and fluorouracil. As discussed above, PAGC has been demonstrated to be effective in improving patients' quality-of-life, where one of the parameters measured was improvement in appetite. This, together with the mouse study, suggests that PAGC could help patients with cachexia, a general physical wasting and malnutrition caused by a chronic disease such as cancer or the therapies for it. Based on the results above and the comparison with PAGC, AMC is expected to show the same benefit.

Combination Therapy with G-CSF in Cancer Patients undergoing Myelosuppressive Therapy to Increase Neutrophil Recovery and to Reduce the use of G-CSF PAGC has been shown to stimulate the production of cytokines especially G-CSF from activated human peripheral blood mononuclear cells, promote recovery of GM-CFC and peripheral WBC counts in radiation-induced myelosuppression animal model, and restore the WBC counts of cancer patients after chemotherapy in a major clinical trial in the People's Republic of China. These results suggest that PAGC may act indirectly on the hematopoiesis system through production of multiple endogenous cytokines and these cytokines may act in synergy to promote neutrophil recovery. PAGC is also shown to have a synergistic effect with IL-3 in promoting the proliferation/maturation of bone marrow megakaryocytes as discussed above. Also, the administration of PAGC was safe and well tolerated, without the adverse reactions seen in the use of G-CSF such as bone pain, muscle ache, headache, fatigue, nausea, vomiting, diarrhea, etc. This, and the synergistic effects discussed above, suggest that PAGC may combine with G-CSF to reduce the use of exogenous G-CSF to promote neutrophil recovery in cancer patients undergoing myelosuppressive therapy. Based on the results above and the comparison with PAGC, AMC is expected to show the same benefit.

Combination Therapy with G-CSF to Accelerate Neutrophil Recovery Following High-Dose Cytotoxic Therapy with Autologous or Allogeneic Blood Progenitor Cell Transplantation High-dose chemotherapy and/or radiotherapy supported by. (marrow or peripheral blood) blood progenitor cell (BPC) transplant is being used to treat a number of cancer patients with conditions such as breast cancer, lymphoma, and multiple myeloma. Transplantation with BPC results in more rapid hematopoietic recovery. G-CSF is often used after BPC transplantation to accelerate neutrophil recovery in order to prevent neutropenic fever associated with infection, to shorten the hospital stay, and to reduce the use of antibiotics. PAGC has been shown to restore cancer patients' WBC counts after chemotherapy; and that together with the pharmacological effects summarized in previous sections suggests that PAGC may also be useful as a combination therapy with G-CSF after BPC transplantation to accelerate neutrophil recovery. Based on the results above and the comparison with PAGC, AMC is expected to show the same benefit.

Biological Response Modifier for Hepatitis B Carriers and Protection of Hepatic Cells Cytokines play an important role in the defense against viral infections. The cytokines produced by cells involved in the immune response, such as macrophages and CD4+ and CD8+T lymphocytes, play a more direct role in recovery from viral infection such as hepatitis B viral (HBV) infection. From animal models and human studies, it is clear that the cellular immune response may play a role in resolution of HBV infection and disease pathogenesis. In acute HBV infection, a vigorous polyclonal cellular immune response is critical. Type 1 cytokine release, characterized by production of IL-2 and IFN-γ by CD4+ T cells, which prime and maintain antigen-specific cellular immunity, is important in defense against viral infection [C. A. Biron, "Cytokines in the generation of immune response to, and resolution of, virus infection", Curr. Opin. Immunol., 6, 530–538 (1994)]. The cytokines released by CD4+ and CD8+cells also play an important role in the downregulation of HBV replication. If there is a defect in the acute response, HBV becomes chronic. These finding suggest that strategies aimed at boosting the type 1 response or the local production of appropriate cytokines within the liver might be useful as therapy for chronic HBV infection [M. J. Koziel, Sem. Liver Disease, 19(2), 157–161 (1999)]. PAGC is prepared from the traditional Chinese medicinal plant Astragalus membranaceus var. mongholicus (AM) and this plant has been used historically to stimulate the immune and hematopoietic systems. It is widely used to treat patients with various ailments, which are similar to the symptoms of chemotherapy- or radiotherapy-induced myelosuppression (thrombocytopenia and anemia in addition to neutropenia). Additionally, AM has been reported to stimulate mouse spleen cell proliferation in a dose-dependent manner in vitro, increase the natural killer (NK) cell activity in spleen cells of animals inoculated with S-180 sarcoma tumor cells, and also increase the activity of cytotoxic T lymphocytes (CTL). The cytokines produced by CTL can mediate control of viral infection in vivo, and the production of IFN-γ and TNF-α by virus-specific CTL can amplify the ability of CTL to clear viral infection [L. G. Guidotti et al., "Cytotoxic T lymphocytes inhibit hepatitis B virus gene expression by a noncytolytic mechanism in transgenic mice", Proc. Natl. Acad. Sci. USA, 91, 764–3768 (1994)]. Furthermore, as shown above, AMC stimulated the production of G-CSF from human PBMC after activation with PHA. These studies suggest that AMC may affect immune function indirectly through modulation of cytokine production. Crude extracts prepared from AM have been used in chronic hepatitis patients to reduce the elevated IgG, to lower ALT value, and to improve patients' immune and liver functions [Y. Liu, "Therapeutic effect of oral solution from Astragalus in the treatment of 70 chronic hepatitis B patients", Jiang Su Chung Yao, 15(12), 38 (1994)]. Furthermore, fractionated AM has been shown to have immunopotentiating activity, as discussed earlier. These suggest that AMC may be used as a biological response modifier for hepatitis B carriers and to protect liver cells.

Vaccine Adjuvant for Hepatitis B Patients

Polysaccharide prepared from Polyporus umbellatus has been used as an adjuvant to hepatitis B vaccine in treating chronic hepatitis B patients. It has been shown to have statistically significant sero-negative conversion of hepatitis B e antigen (HBeAg) and disappearance of hepatitis B viral DNA (HBV-DNA) [S. M. Wu et al., "The therapeutic observation on the combined Polyporus polysaccharide with hepatitis B vaccine in the treatment of chronic hepatitis B". J. Chin. Infectious Disease, 13(3), 187–189 (1995); H. Z. Shu et al., "The therapeutic observation on the Polyporus polysaccharide with large dose of hepatitis B vaccine in the treatment of 64 cases of chronic hepatitis B patients", Med. J. NDFSC, 6(4), 211–212 (1996)]. Extracts prepared from AM also has been reported to have sero-negative conversion of HBeAg and anti hepatitis B core antigen (anti HBc), and elimination of HBV-DNA in hepatitis B patients [C. K. Liu et al, "Clinical and experimental studies on effects of chronic hepatitis B treated with Astragali composita", Chung Kuo Chung Hsi I Chieh Ho Tsa Chih, 16(7), 394–397 (1996); P. L. Chen et al., "Polysaccharide from Astragalus in treating 33 cases of chronic active hepatitis B patients", New Drugs Clin. Remedies, 11(2), 75–76 (1991)]. These studies and the results discussed above suggest that AMC may be useful as a hepatitis B vaccine adjuvant for hepatitis B patients.

Treatment of withdrawal Symptoms for Narcotic Drug Rehabilitation

When patients are removed from narcotics, they suffer from symptoms of addiction withdrawal. The attributes of withdrawal in traditional Chinese medicine (TCM) terms are manifestation of qi (energy) deficiency. Based on Chinese physicians' observations that it would speed up rehabilitation if the qi could be fortified, one of the indications for PAGC in the human cancer chemotherapy trial is to improve the quality-of-life of cancer patients after chemotherapy. The quality-of-life was assessed by improvement on symptoms associated with chemotherapy; these include lassitude and fatigue, malaise, sweating, shortness of breath and lack of appetite. These symptoms correspond to "qi deficiency syndrome", which is also associated with narcotic withdrawal according to TCM physicians. This suggests that PAGC is able to fortify patients' qi and has pharmaceutical potential for treating addiction withdrawal from narcotics. Based on the results above and a comparison with PAGC, AMC is expected to offer the same benefit.

Prevention and Treatment of Emesis in Cancer Patients on Chemotherapy or Radiation Therapy Nausea and vomiting is a common side effect of chemotherapy and/or radiation therapy. Although there are many improvements with chemotherapy or radiation therapy, a significant number of patients still experience emesis, and efforts to reduce this side effect of treatment must continue. There are many antiemetic drugs (such as serotonin receptor antagonists, corticosteroids, and dopamine receptor antagonists) available to prevent these side effects, however, they have their own side effects. Symptoms that have been associated with these drugs are light headache, constipation, trouble sleeping, restlessness, involuntary movements of the muscles and tongue, and sedation. Although the neuropharmacologic basis of emesis is still incompletely understood, the goals related to the complete control of emesis include providing care that is convenient for the patient, treatment that reduces hospitalization and time in the ambulatory setting, and therapy that enhances the patient's quality-of-life. The PAGC trial demonstrated that PAGC is beneficial to patients after chemotherapy, especially in improving patients' quality-of-life. Observations from the investigators and patients all support that PAGC can really improve the overall well-being of the patients, and this suggests that PAGC may have a role in preventing and treating emesis after chemotherapy. Based on the results above and a comparison with PAGC, AMC is expected to offer the same benefit.

Reduction in or Replacement of the use of Erythropoietin for Kidney Dialysis Patients EPOGEN (epoetin alfa, erythropoietin) was approved in 1989 for treatment of the anemia associated with chronic renal failure in patients receiving dialysis. This provides a means for these patients to lead more active, productive lives. Prior to the availability of EPOGEN, 90% of all dialysis patients suffered from anemia, leaving them fatigued and exhausted and impairing their ability to work. Today, most patients undergoing dialysis receive EPOGEN as part of their treatment regimen to elevate and maintain red blood cell levels. In clinical trials, the most frequently reported adverse events with EPOGEN were hypertension, headache, seizures, nausea/vomiting, and clotted vascular access; and it is recommended to reduce the dose of EPOGEN if these side effects occur. Studies of AMC indicated that it could promote the recovery of peripheral red blood cell counts in sublethally irradiated mice as shown in Example 7; and PAGC has shown the same benefit. In addition, PAGC has been shown to increase the numbers of circulating BFU-E when administrated as a single agent and synergized with G-CSF to increase the numbers of circulating BFU-E in-normal mice, and to increase the number of TER-119$^+$ cells in peripheral blood of both normal and cyclophosphamide-treated mice. The TER-119 antigen is expressed on erythroid cells from the early erythroblast through mature erythrocyte stages. An increase in the number of TER-119$^+$ cells indicates that PAGC could stimulate the differentiation, proliferation and maturation of the erythroid lineage in the bone marrow, and the mobilization of these cells to the peripheral blood. All these findings suggest that PAGC can promote the production and maturation of red blood cells in the mice studied. Further, PAGC has been shown to be safe, with no clinically significant adverse events reported, in a human clinical trial. Based on the results and the comparison with PAGC, it is therefore suggested that AMC may be able to reduce or even replace the use of EPOGEN for treatment of anemia in kidney dialysis patients.

In conclusion, AMC administered in a similar manner as PAGC promoted white blood cell, red blood cell, and platelet recovery with improvement over control in irradiated mice; demonstrating the same benefit in this model as that given by PAGC; and suggesting, when taken with the other PAGC data discussed in this application, that AMC has the same therapeutic benefits as PAGC, and is therefore suitable for the same utilities and pharmaceutical indications as PAGC.

Pharmaceutical Formulations and Administration

In general, the acid-modified arabinogalactan protein composition of the first aspect of this invention will be administered in therapeutically effective amounts by intravenous injection, either singly or in conjunction with of at least one other therapeutic agent, especially a therapeutic agent capable of stimulating hematopoiesis. A therapeutically effective amount may vary widely depending on the disease, its severity, the age and relative health of the animal being treated, and other factors. For stimulating hematopoiesis, inducing the proliferation or maturation of megakaryocytes, stimulating the production of IL-1β, IL-6, TNF-α, IFN-γ, GM-CSF, or G-CSF, stimulating the production or action of neutrophils, treating neutropenia, anemia, or thrombocytopenia, or accelerating recovery from exposure (e.g. accidental or non-therapeutic exposure, as well as therapeutic exposure) to cytotoxic agents or radiation, a therapeutically effective amount of the purified arabinogalactan composition of the first aspect of this invention ranges about between 10 and 1000 mg/day, particularly about between 50 and 500 mg/day, especially about between 100 and 250 mg/day, for a human of average body mass. For treating cachexia, emesis, or drug withdrawal symptoms, or modifying biological responses or protecting hepatic cells in hepatitis B, a similar amount will be therapeutically effective. A person of ordinary skill in the art will be able without undue experimentation, having regard to that skill and this disclosure, to determine a therapeutically effective amount of the compositions of this invention for a given disease.

In general, the acid-modified arabinogalactan protein composition of the first aspect of this invention will be administered as a pharmaceutical formulation by injection. The formulation will comprise the acid-modified arabinogalactan protein composition of the first aspect of this invention in combination with an aqueous injectable excipient. Suitable aqueous injectable excipients are well known to persons of ordinary skill in the art, and they, and the methods of formulating the formulations, may be found in such standard references as Alfonso AR: Remington's Pharmaceutical Sciences, 17th ed., Mack Publishing Company, Easton Pa., 1985. Suitable aqueous injectable excipients include water, aqueous saline solution, aqueous dextrose solution, and the like, optionally containing dissolution enhancers for the acid-modified arabinogalactan protein composition, such as 3–10% mannitol or other sugars, 3–10% glycine or other amino acids.

Typically, when administered as a hematopoietic agent, the acid-modified arabinogalactan protein composition of the first aspect of this invention or the acid-modified arabinogalactan protein formulation of the second aspect of this invention will be administered by injection (subcutaneously, intramuscularly, intraperitoneally, intravenously, etc., especially intravenously), especially by continuous intravenous infusion over a period of a few minutes to an hour or more, such as around fifteen minutes. The amount of the acid-modified arabinogalactan protein composition of this invention in the formulation may vary widely depending on the type of formulation, size of a unit dosage, kind of excipients, and other factors well known to those of ordinary skill in the art. In general, the final formulation may comprise from 0.001 percent by weight (% w) to 10% w of the acid-modified arabinogalactan protein composition of this invention, preferably 0.01% w to 1% w, with the remainder being the excipient or excipients.

The acid-modified arabinogalactan protein composition of the first aspect of this invention may optionally be administered in conjunction with at least one other therapeutic agent for the disease state being treated, especially another agent capable of stimulating hematopoiesis such as, for example, erythropoietin, thrombopoietin, granulocyte colony stimulating factor (G-CSF), IL-3, and the like.

EXAMPLES

The following non-limiting examples illustrate the invention. All acid-modified arabinogalactan protein compositions were characterized by size exclusion chromatography.

The size exclusion chromatography method was as follows:

A Shimadzu HPLC system, equipped with an SCL-10A system controller, LC-10AD pump, DGU-4A degasser, RID-6A refractive index detector, and SPD-10AV UV detector, and using GS-701 and GS-620 columns (Shodex Asabipak, 7.6×500 mm) equilibrated with 0.2 N sodium chloride. The sample amount loaded was 80 μg (40 μL of sample solution at 2 mg/mL in water), and samples were eluted at 1 mL/min. Pullulan standards with different average molecular weight were used to prepare a calibration curve;

and the molecular weights were determined from the calibration curve. The weight average molecular weight (Mw=Σ($A_i M_i$)/Σ$A_i$), number average molecular weight (Mn=Σ$A_i$/Σ($A_i$/$M_i$)), and polydispersity (Mw/Mn) of a sample was determined by statistical calculation using the Shimadzu SEC software, Version 2.4.

The sugar content and composition of the acid-modified arabinogalactan protein composition of this invention was determined by GLC analysis of the trimethylsilyl methyl glycoside derivatives. In this method, the sample was first methanolyzed in methanolic HCl, followed by a trimethylsilyl (TMS) derivatization to generate volatile monosaccharide derivatives. After a clean-up, the derivatives were analyzed by Gas Liquid Chromatography (GLC) using a DB-1 column with a Flame Ionization Detector (FID). An internal standard, myo-inositol, was derivatized and analyzed together with the composition sample to quantitate the sugar content and composition.

Hydroxyproline content was determined by a colorimetric assay. The sample was first hydrolyzed with hydrochloric acid, then treated with sodium hypobromite (a solution of bromine in sodium hydroxide), hydrochloric acid, and dimethylaminobenzaldehyde. The optical density of the final solution was measured on a colorimeter, with the hydroxyproline content determined from a calibration curve made from hydroxyproline of various concentrations prepared in the same manner.

Example 1

Preparation of the Acid-Modified Arabinogalactan Composition, with Acid Treatment as the Last Step Step A. "Drink Chip" Processing Dried *Astragalus membranaceus* roots, 300 Kg, were processed into drink chips by removing any contaminated parts, sterile washing and scrubbing with ultrafiltered water, soaking in 70% ethanol overnight, cutting into chips with a thickness of 3–5 mm, and sterile oven drying at 60–70° C. These dried "drink chips" have a loss on drying of <15%.

Step B. Crude Arabinogalactan Composition Extraction

"Drink chips", 2 Kg, produced in Step A, are washed with 10 L of 0.5 M $KH_2PO_4$ (pH 4.5 at 25° C.) for 30 minutes at a temperature near 100° C., and the wash solution is discarded. They are then extracted once with 20 L 0.5 M $KH_2PO_4$ (pH 4.5 at 25° C.) and twice with 20 L endotoxin-free water (deionized water ultrafiltered through a 10K MWCO UF system) at 100° C., each time for three hours. The pooled aqueous extract is clarified by filtration or centrifugation at approximately 7500×g for about 30 minutes, then is concentrated about 12-fold by ultrafiltration using a 100K MWCO polyethersulfone membrane which has been depyrogenated with hot alkali. Ethanol, 95%, is added to the concentrate to give a final ethanol concentration of 35%, with stirring at room temperature for fifteen minutes, to precipitate poorly soluble materials. The precipitate is removed by filtration or centrifugation, and the supernatant carried through into the next step, where sufficient 95% ethanol is added to being the ethanol concentration to 70%, to precipitate the arabinogalactan proteins, which are recovered by filtration or centrifugation at approximately 7500×g. The precipitate is stable in 70% ethanol and may be maintained in this form if required. The precipitate is re-dissolved in UF water to a concentration of about 20 g/L, and dried (spray-dried, tray-dried, or lyophilized) to generate the crude arabinogalactan composition.

The crude arabinogalactan composition is a light-yellow powder, soluble in water at 200 mg/mL, and has a loss on drying of <15%. The endotoxin content is <0.3 EU/mg.

Step C. Purification by Ion-Exchange Chromatography

The crude arabinogalactan composition, 35 g, from Step B is dissolved in 20 mM NaOAc buffer concentration at pH 5.2 to about 40 g/L. The solution is loaded onto an SP Sepharose cation exchange column (about 20 mL resin, equilibrated with the same buffer, per 1 g of crude AGC) and eluted with 20 mM NaOAc, collecting 2.5–3.0 bed volumes of the eluate. The collected eluate is loaded onto a Q Sepharose anion exchange column with the same resin volume as the SP column and eluted with 20 mM NaOAc, collecting 3–3.5 bed volumes of the eluate. The collected eluate is ultrafiltered with a 100K MWCO UF system to desalt and concentrate it to about 40 g/L. The retentate may be precipitated by addition of anhydrous ethanol to a final ethanol concentration of 80–90%, or may be used directly in the next step.

The arabinogalactan protein composition is a white powder, soluble in water, saline, and 5% glucose at 20 mg/mL, with an aqueous solution having a pH between 4 and 7. The composition contains ≦0.5 EU/mg of endotoxin, and ≦10 ppm of heavy metals. It has an Ara:Gal ratio of ≧3.0:1, typically ≧4.0:1. The weight average molecular weight of the composition is ≧100 kiloDaltons.

Step D. Acid Modification and Isolation

The arabinogalactan protein composition retentate from Step C is mixed with an equal volume of 1 M HCl. The resulting solution, 0.5 M in HCl, is incubated for 6 hours at 30° C., and then neutralized with 1 M NaOH. The neutral solution containing the acid-modified arabinogalactan protein composition is desalted by ultrafiltration through a 100K MWCO Biomax 100 membrane, chasing with endotoxin-free water, and reconcentrated to about 20 g/L.

The resulting solution my be lyophilized directly or after dispensing into single-dose vials, especially after the addition of dissolution-enhancing excipients such as mannitol or other sugars, glycine or other amino acids, or sodium chloride.

The acid-modified arabinogalactan protein composition is a white to off-white powder, with an Ara:Gal ratio of not more than 3.5:1; an ash content of not more than about 2% by weight, a heavy metal content of not more than about 20 ppm by weight; substantially free of endotoxin; with a weight average molecular weight between 120 and 260 kiloDaltons; and soluble in water to at least 200 mg/mL.

Example 2

Preparation of the Acid-Modified Arabinogalactan Composition, with Sequential Ion-Exchange Chromatography as the Last Step Step B. Crude Arabinogalactan Protein Composition Extraction "Drink chips", 150 g, produced in Step A of Example 1, were extracted three times with 1.5 L of endotoxin-free 0.5 M $KH_2PO_4$, pH 4.5, by refluxing at 100° C. for 3 hours. The combined extracts were concentrated to 200 mL and simultaneously exchanged into endotoxin-free water by ultrafiltration through a 100K MWCO Biomax 100 polyethersulfone UF membrane (Millipore Corp.). To the concentrate is added 95% ethanol, with stirring, to a final ethanol concentration of 35% v/v to precipitate undesired materials. The ethanol suspension is centrifuged at 8000×g, and the precipitate is discarded. The supernatant is further diluted with 95% ethanol, with stirring, to a final ethanol concentration of 70% v/v, resulting in the formation of a second precipitate. This second precipitate, containing the crude arabinogalactan protein composition, is harvested by high-speed centrifugation at 8000×g and dried at 60–70° C. in a sterile oven [note that the precipitate here can be taken into Step c without intermediate drying if desired].

Step C. Acid Modification

The dried crude arabinogalactan protein compositions from Step B is dissolved in endotoxin-free water to a concentration of 40 mg/mL and then mixed with an equal volume of 1 M hydrochloric acid. The resulting solution, 0.5 Min HCl, is incubated for 6 hours at 30° C., and then neutralized with 1 M NaOH. The neutral solution containing the acid-modified arabinogalactan protein composition is desalted and freed of low molecular weight materials by ultrafiltration through a 100K MWCO Biomax 100 membrane, chasing with endotoxin-free water.

Step D: Purification by Ion Exchange Chromatography and Isolation

The retentate from Step C is made 20 mM in NaOAc, pH 5.2, and then passed through, in succession, a cation-exchange column packed with SP-Sepharose (1.5 cm×25 cm), and an anion-exchange column packed with Q-Sepharose (1.5 cm×25 cm). The eluate from the anion-exchange column contains the acid-modified arabinogalactan protein composition. The eluate is desalted by ultrafiltration through a 100K MWCO Biomax 100 membrane, and the acid-modified arabinogalactan protein composition is recovered by lyophilization.

Example 3

Preparation of the Acid-Modified Arabinogalactan Composition, with Ion Exchange in Batch Mode as the Last Step The process of Example 2, Steps B and C, is used to prepare a desalted solution containing the acid-modified arabinogalactan protein composition.

Step D. Purification by Ion Exchange in Batch Mode and Isolation.

The retentate from Step C is stirred with 1 g IONAC NM-60 mixed-bed ion-exchange resin for 1 hour at room temperature. The resin is removed by filtration and the filtrate, containing the acid-modified arabinogalactan protein composition, is desalted by ultrafiltration through a 100K MWCO Biomax 100 membrane, then lyophilized to dryness.

A similar result is obtained by sequential batch stirring of the retentate from Step D with cation- and anion-exchange resins instead of using a mixed-bed resin.

Example 4

Preparation of the Acid-Modified Arabinogalactan Composition, with Acid Treatment as the Last Step and Ion-Exchange in Batch Mode as the Penultimate Step The process of Example 1 is followed, substituting ion exchange in batch mode as described in Step D of Example 3 for the ion-exchange chromatography of Step C of Example 1.

Example 5

Production of Cytokines from Activated Human Peripheral Blood Mononuclear Cells

Human peripheral blood mononuclear cells (PBMC) were prepared using the method of Boyum [A. Boyum, "Isolation of mononuclear cells and granulocytes from human blood . . . ", Scan. J. Lab. Invest., 97, 77–89 (1968)]. Human blood buffy coat samples, approximately 25 mL/donor, were obtained from the Stanford University Medical Center Blood Bank. Using sterile techniques, each buffy coat samples was gently resuspended in a total volume of 100 mL with the addition of calcium- and magnesium-free Hank's balanced salt solution (HBSS, Gibco) at room temperature. A volume of 25 mL of the cell suspension was then layered onto 15 mL of Ficoll-Paque (Pharmacia LKB Biotechnology, Inc.) in a 50 mL conical centrifuge tube, and the tube was centrifuged in a Beckman GPR tabletop centrifuge (GH-3.7 rotor) at 400×g for 30 minutes at 15° C. Following centrifugation, the PBMC suspension at the interface was transferred to a new 50 mL tube, resuspended in a total volume of 45 mL HBSS, and centrifuged at 354×g for 10 minutes at 15° C. The supernatant was discarded, the cell pellets was resuspended to a total of 45 mL with HBSS, and centrifuged again at 265×g for 10 minutes at 15° C. The cell pellet was resuspended in 10 ml of X-Vivo tissue culture medium (Bio Whittaker, MD) and counted using a hemocytometer. Polystyrene tubes (Falcon #2057, Becton Dickinson) were used in the following experiment. PBMC suspensions were diluted to $4 \times 10^6$/nL; 1 nm was incubated in the presence of 0.5 mL phytohemagglutinin P (PHA-P, Pharmacia 27-3707-01) at a final concentration of 3 µg/mL together with 0.5 mL of a solution of the composition of this invention at various concentrations. Comparator solutions contained (1) a purified arabinogalactan composition (PAGC) that was prepared by extraction of "drink chips", ethanol precipitation, purification by ion exchange chromatography, and further ethanol precipitation; or (2) an arabinogalactan protein composition (AGPC) that was prepared by extraction of "drink chips", ethanol precipitation, purification by ion exchange chromatography, ultrafiltration of the ion-exchange eluate with a 100K MWCO UF membrane (keeping the retentate), and further ethanol precipitation. The total volume per tube was 2 mL. After 24 hours incubation at 37° C. in a incubator with 7% $CO_2$, the tubes were centrifuged in a Beckman GPR tabletop centrifuge (GH-3.7 rotor) at 1600×g for 10 minutes at 15° C., and the supernatants were collected and stored at −70° C. prior to assay. Cytokine measurements were carried out using commercially available ELISA assay kits for human G-CSF (R&D Systems, MN, or Pharmingen) in accordance with the manufacturer's protocols. Optical density was determined using a microplate reader (Thermo max, Molecular Devices, CA). Results were calculated using the software provided with the microplate reader and expressed as µg/mL of G-CSF produced in the supernatants. The following table shows that AMC increased G-CSF production by activated human PBMC, and was superior to both the PAGC and the AGPC. Student's t-testing of the results showed that AMC was superior to PAGC at concentrations from 10 to 300 µg/mL, and superior to AGPC at concentrations from 10 to 1000 µg/mL ($p<0.02$). The greatest difference (ratio of G-CSF induced with AMC to G-CSF induced with PAGC) occurred at 10 µg/mL (4.5:1), and it remained evident at up to 100 µg/mL (2.5:1); though at higher concentrations, a smaller difference was seen.

| Test composition, | G-CSF, pg/mL, mean (standard deviation) | | |
|---|---|---|---|
| (µg/mL) | PAGC | AGPC | AMC |
| 0 | 63 (118) | 97 (233) | 143 (370) |
| 3 | 92 (171) | 137 (314) | 193 (349) |
| 10 | 163 (223) | 242 (486) | 741 (1110) |
| 30 | 512 (726) | 618 (924) | 1812 (2376) |
| 100 | 1154 (1604) | 1404 (1789) | 2882 (2740) |
| 300 | 2091 (2414) | 2390 (2180) | 3587 (2907) |
| 1000 | 3382 (2978) | 2378 (1810) | 4038 (2855) |

Example 6

Recovery of Peripheral Blood in Sublethally Irradiated Mice

Female BALB/c mice with an average body weight of 20 grams, 9–14 weeks old, were used for the study. Five days before each experiment, Neomycin (Sigma, St. Louis, Mo.), 40 mg/L, was added to non-acidified drinking water. Mice were randomly assigned to control or treated group, 6 mice per group, and were irradiated were irradiated with 5 Gy of X-rays (250 KVP, 1.6 mm Al filter, Philips) on day 0. Following this dose of irradiation, the peripheral blood leukocyte and platelet counts are significantly lower than that of normal mice, and the erythrocyte count is moderately lower. The acid-modified arabinogalactan protein composition was given by subcutaneous injection at 250, 100, and 50 mg/Kg. Treatments were given each for the first 5 days (from day 0 to day 4), and then 3 times a week for the next 3 weeks (days 7–10, 14–16, and 21–23), with the first dose given 4–5 hours after irradiation. A total of 14 doses of acid-modified arabinogalactan protein composition were administered. The control group was given 0.1 mL saline subcutaneously. Mice were bled through the orbital vein on days 9, 13, 16, and 20 during the experiment; blood samples were collected into EDTA-coated tubes (Sarstedt, Germany); and peripheral blood platelets and red blood cells were analyzed in a Serono 9010+ cell counter (Serono Baker Diagnostics Inc., Allentown, Pa.). Acid-modified arabinogalactan protein composition at 250, 100, and 50 mg/Kg promoted both red blood cell and platelet recovery with improvement over control in irradiated mice at all points post-irradiation, as shown in the tables below.

| | Average red blood cell count, $10^9$/mL | | | | |
|---|---|---|---|---|---|
| Days after irradiation | 0 | 9 | 13 | 16 | 20 |
| AMC, 250 mg/Kg | 9.55 | 10.2 | 7.63 | 5.79 | 7.62 |
| AMC, 100 mg/Kg | 9.55 | 9.66 | 7.25 | 6.09 | 7.61 |
| AMC, 50 mg/Kg | 9.55 | 9.38 | 6.90 | 6.27 | 7.38 |
| Saline | 9.55 | 7.97 | 6.70 | 5.40 | 6.64 |

| | Average platelet count, $10^6$/mL | | | | |
|---|---|---|---|---|---|
| Days after irradiation | 0 | 9 | 13 | 16 | 20 |
| AMC, 250 mg/Kg | 935 | 141 | 212 | 415 | 734 |
| AMC, 100 mg/Kg | 935 | 166 | 196 | 357 | 624 |
| AMC, 50 mg/Kg | 935 | 149 | 221 | 416 | 671 |
| Saline | 935 | 131 | 132 | 270 | 570 |

PAGC at doses of 100 and 300 mg/Kg is statistically significantly better than saline, and AGPC at 100 and 250 mg/Kg is better than saline (statistical significance not determined), in this assay.

In a similar experiment, acid-modified arabinogalactan protein composition was shown to increase the speed of recovery (white blood cell count returning to at least $8 \times 10^6$/mL) dramatically over saline alone: an average of 21 days to recovery for the AMC-treated group, whereas only 1 of 7 mice in the saline group had recovered by day 30; and increase the speed of recovery over PAGC, with a speed similar to that seen for AGPC.

While this invention has been described in conjunction with specific embodiments and examples, it will be apparent to a person of ordinary skill in the art, having regard to this disclosure, that equivalents of the specifically disclosed materials and techniques will also be applicable to this invention; and such equivalents are intended to be included within the following claims.

What is claimed is:

1. An acid-modified arabinogalactan protein composition, having an arabinose:galactose ratio of less than 3.5:1, comprising 5–10% Rha, 20–35% Gal, and less than 5% Glc, prepared from *Astragalus membranaceus*.

2. The acid-modified arabinogalactan protein composition of claim 1 prepared from the roots of *Astragalus membranaceus*.

3. The acid-modified arabinogalactan protein composition of claim 1 where the *Astragalus membranaceus* is *A. membranaceus* Bge. var. *mongholicus* (Bge.) Hsiao or *A. membranaceus* (Fisch.) Bge.

4. The acid-modified arabinogalactan protein composition of claim 1 that is prepared from *Astragalus membranaceus* grown in Inner Mongolia or Shanxi province, Peoples' Republic of China.

5. The acid-modified arabinogalactan protein composition of claim 1 where the *Astragalus membranaceus* comprises two-year old *Astragalus membranaceus* plants.

6. The acid-modified arabinogalactan protein composition of claim 1 having a weight average molecular weight of at least 100 kiloDaltons.

7. The acid-modified arabinogalactan protein composition of claim 1 comprising at least 80% by weight carbohydrate and not more than 2% by weight protein.

8. The acid-modified arabinogalactan protein composition of claim 1 having an arabinose:galactose ratio of less than 3.0:1.

9. The acid-modified arabinogalactan protein composition of claim 1 having an endotoxin content of not more than 1.0 EU/mg by Endospecy assay.

10. The acid-modified arabinogalactan protein composition of claim 1 having a pH when reconstituted between 4 and 7.

11. An aqueous injectable acid-modified arabinogalactan protein formulation comprising:
    (a) a therapeutically effective amount of the acid-modified arabinogalactan protein composition of claim 1; and
    (b) an aqueous injectable excipient.

12. A method of stimulating the immune and/or hematopoietic system of a mammal by administration of the acid-modified arabinogalactan protein composition of claim 1, comprising administering to the mammal an effective amount of the acid-modified arabinogalactan protein composition of claim 1.

13. The method of claim 12 where the method of stimulating the immune and/or hematopoietic system of a mammal is selected from the group consisting of stimulating hematopoiesis, inducing the proliferation of megakaryocytes, inducing the maturation of megakaryocytes, stimulating the production of IL-1β, stimulating the production of IL-6, stimulating the production of TNF-α, stimulating the production of IFN-γ, stimulating the production of GM-CSF, stimulating the production of G-CSF, stimulating the production of neutrophils, stimulating the action of neutrophils, stimulating the immune and/or hematopoietic system of a mammal suffering from neutropenia, stimulating the immune and/or hematopoietic system of a mammal suffering from anemia, stimulating the immune and/or hematopoietic system of a mammal suffering thrombocytopenia, stimulating the immune and/or hematopoietic system of a mammal suffering from exposure to cytotoxic agents, stimulating the immune and/or hematopoietic system of a mammal suffering from exposure to radiation, stimulating the immune and/or hematopoietic system of a mammal suffering from cachexia, stimulating the immune and/or hematopoletic system of a mammal suffering from emesis, stimulating the immune and/or hematopoietic system of a mammal suffering from drug withdrawal symptoms, stimulating the immune and/or hematopoletic system of a mammal suffering from infection, stimulating the immune response to infection, stimulating the immune and/or hematopoietic system of a mammal suffering from an immunosuppressive condition, stimulating the immune response in immunosuppressive conditions, and stimulating the immune and/or hematopoietic system of a mammal suffering from hepatitis B.

14. The method of claim 13 where the method of stimulating the immune and/or hematopoietic system of a mammal is selected from the group consisting of stimulating hematopoiesis, inducing the proliferation of megakaryocytes, inducing the maturation of megakaryocytes, stimulating the production of IL-1β, stimulating the production of IL-6, stimulating the production of TNF-α, stimulating the production of IFN-γ, stimulating the production of GM-CSF, stimulating the production of G-CSF, stimulating the production of neutrophils, stimulating the action of neutrophils, stimulating the immune and/or hematopoietic system of a mammal suffering from neutropenia, stimulating the immune and/or hematopoietic system of a mammal suffering from anemia, and stimulating the immune and/or hematopoietic system of a mammal suffering from thrombocytopenia.

15. The method of claim 12 where the mammal is a human.

16. The method of claim 15 where the human is suffering from bone marrow suppression.

17. The method of claim 16 where the bone marrow suppression is the result of cancer chemotherapy or radiation therapy.

18. The method of claim 12 further comprising the administration of at least one additional therapeutic agent.

19. The method of claim 18 where the at least one therapeutic agent is a therapeutic agent capable of stimulating hematopoiesis.

20. The method of claim 19 where the at least one therapeutic agent is selected from the group consisting of erythropoietin, thrombopoietin, granulocyte colony stimulating factor, granulocyte-macrophage colony stimulating factor, and interleukin-3.

21. A method of preparing the acid-modified arabinogalactan protein composition of claim 1, comprising:
   (a) treating an arabinogalactan protein composition extracted from *Astragalus membranaceus* with an aqueous acid to cause truncation of the arabinogalactan branches of the arabinogalactan protein component of the composition and reduce the arabinose:galactose ratio to less than 3.5:1; and
   (b) purifying the product from step (a) to isolate the acid-modified arabinogalactan protein composition.

22. The method of claim 21 where the aqueous acid is hydrochloric acid.

23. A method of preparing the acid-modified arabinogalactan protein composition of claim 1, comprising:
   (a) purifying an arabinogalactan protein composition extracted from *Astragalus membranaceus*; and
   (b) treating the product from step (a) with an aqueous acid to cause truncation of the arabinogalactan branches of the arabinogalactan protein component of the composition and reduce the arabinose:galactose ratio to less than 3.5:1, and isolating the resulting acid-modified arabinogalactan protein composition.

24. The method of claim 23 where the aqueous acid is hydrochloric acid.

* * * * *